Figure 1:
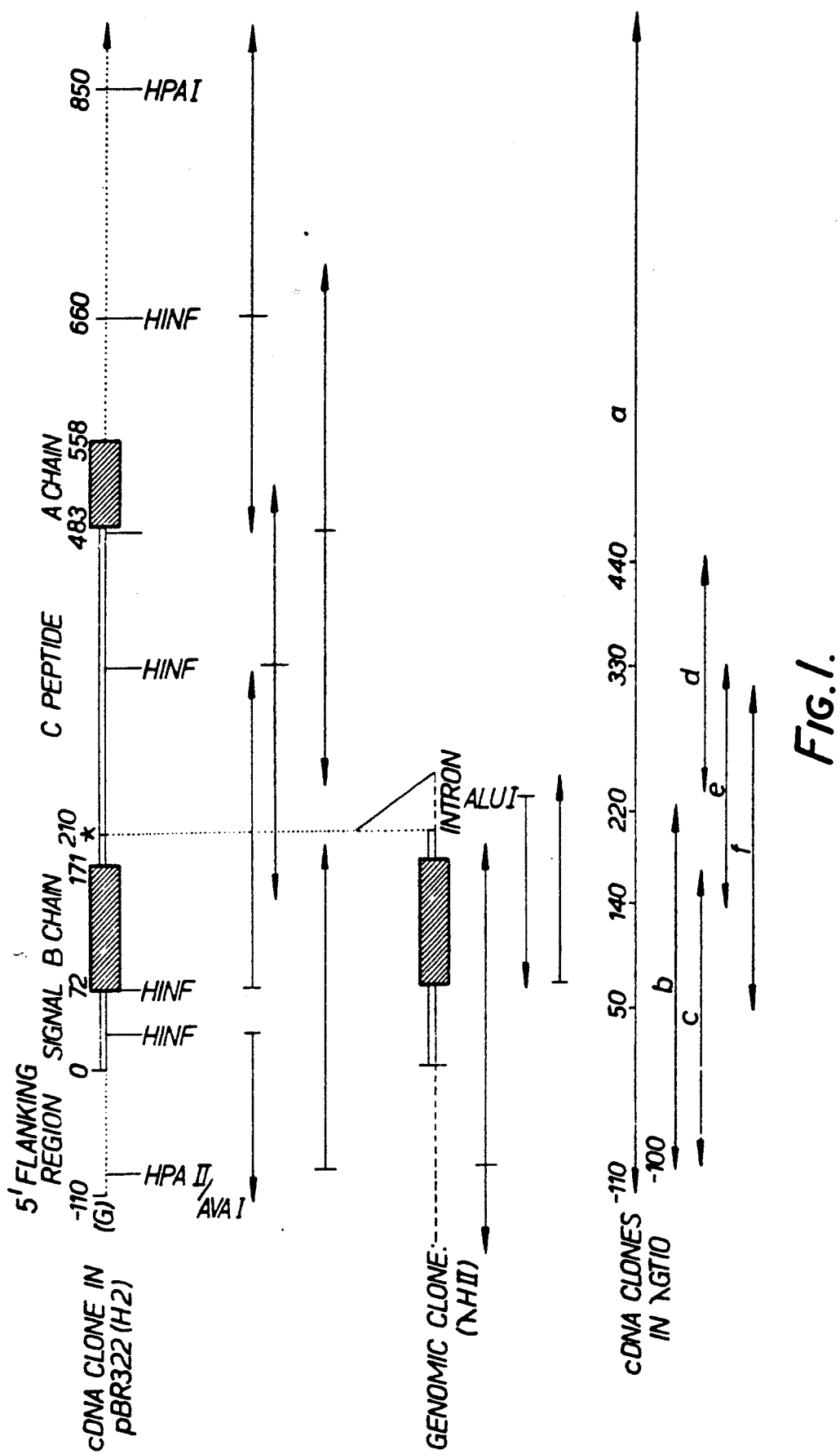

United States Patent [19]

Hudson et al.

[11] Patent Number: 5,326,694

[45] Date of Patent: * Jul. 5, 1994

[54] PROCESS FOR SYNTHESIZING HUMAN H2-PRORELAXIN, HUMAN H2-RELAXIN AND FUSION PROTEINS THEREOF

[75] Inventors: Peter J. Hudson, Bulleen; Hugh D. Niall, Elwood; Geoffrey W. Tregear, Hawthorn, all of Australia

[73] Assignee: Howard Florey Institute of Experimental Physiology and Medicine, Victoria, Australia

[*] Notice: The portion of the term of this patent subsequent to Jul. 19, 2005 has been disclaimed.

[21] Appl. No.: 871,318

[22] Filed: Apr. 20, 1992

Related U.S. Application Data

[60] Continuation of Ser. No. 665,129, Mar. 6, 1991, Pat. No. 5,179,195, which is a division of Ser. No. 21,885, Mar. 4, 1987, Pat. No. 5,023,321, which is a division of Ser. No. 560,790, Dec. 13, 1983, Pat. No. 4,758,516.

[30] Foreign Application Priority Data

Dec. 13, 1982 [AU] Australia ............... PF/7247/82

[51] Int. Cl.$^5$ .............. C12N 15/00; C07K 7/10
[52] U.S. Cl. .................. 435/69.4; 530/324; 530/303; 435/69.7; 435/320.1
[58] Field of Search ............. 530/303, 324; 435/69.4, 435/69.7, 320.1

[56] References Cited

U.S. PATENT DOCUMENTS

| | | | |
|---|---|---|---|
| 4,267,101 | 5/1981 | Bagazzi . | |
| 4,468,464 | 8/1984 | Cohen et al. | 435/317 |
| 4,624,804 | 11/1986 | Voelter et al. . | |
| 4,656,249 | 4/1987 | Tregear et al. | 530/324 |
| 4,871,670 | 10/1989 | Hudson et al. | 435/172.3 |

FOREIGN PATENT DOCUMENTS 0026598 4/1981 European Pat. Off. .
0068375 1/1983 European Pat. Off. .

OTHER PUBLICATIONS

Fields, J. Clin. Endocrinol. Metabol., 52(1):79–85 (1981).
Haley et al, DNA, 1(2):155–162 (1982).
Chemical Abstracts, 97:727496 (1982).
Johnston et al, in "Peptides, Structure and Function", Proc. Ninth Amer. Peptide Symposium (Ed. Deber et al), Pierce Chemical Co., Rockford, Ill., pp. 683–686 (1985).
Dodson et al, Int. J. Biol. Macromol., 4:399–405 (1982).
Blundell et al, in "Biology of Relaxin and Its Role in the Human" (Bigazzie et al, Eds.), Exerpta Medica, Amsterdam, pp. 14–21 (1938).
Isaacs et al, Nature, 271:278–281 (1978).
Hudson et al, Nature, 291:137–131 (1981).
Weiss et al, Science, 194:948–949 (1976).
Hudson et al, Nature, 301:628–631 (1983).
Chemical Abstracts, 96:194404 (1980).
James et al, Nature, 267:544–546 (1977).
Suggs et al, Proc. Nat'l Acad. Sci., 78(11):6613–6617 (1981).
Maniatis et al, Molecular Cloning: A Laboratory Manual, Cold Spring Harbor Laboratory, pp. 422 and 427 (1982).

Primary Examiner—Robert J. Hill, Jr.
Assistant Examiner—Sally P. Teng
Attorney, Agent, or Firm—Sughrue, Mion, Zinn, Macpeak & Seas

[57] ABSTRACT

Genes and DNA transfer vectors for the expression of human preprorelaxin; sub-units thereof, including genes and transfer vectors for expression of human prorelaxin and the individual A, B and C peptide chains thereof; and equivalents of all such genes. Methods for synthesis of the peptides involving recombinant DNA techniques.

6 Claims, 10 Drawing Sheets

```
┌─────Signal peptide─────────────────▶
                              -20
      Met Pro Arg Leu Phe │Phe│Phe His Leu Leu │Gly Val│Cys Leu
   H2 AUG CCU CGC CUG UUU │UUU│UUC CAC CUG CUA │GGA GUC│UGU UUA
      *** *** *** *** **  │ **│*** *** *** *** │*** ** │*** ***
   H1 AUG CCU CGC CUG UUC │UUG│UUC CAC CUG CUA │GAA UUC│UGU UUA
      Met Pro Arg Leu Phe │Leu│Phe His Leu Leu │Glu Phe│Cys Leu 10
   │Met Glu Glu│Val Ile Lys Leu Cys Gly Arg Glu Leu Val Arg
   │AUG GAG GAA│GUU AUU AAA UUA UGC GGC CGC GAA UUA GUU CGC
   │ *  *  **  │ ** *** *** *** *** *** *** *** *** *** ***
   │AAG GAC GAU│GUU AUU AAA UUA UGC GGC CGC GAA UUA GUU CGC
   │Lys Asp Asp│Val Ile Lys Leu Cys Gly Arg Glu Leu Val Arg 30          C-peptide               40
    Arg Ser Leu│Ser Gln Glu Asp Ala Pro Gln Thr Pro Arg Pro
    AGG UCU CUG│AGC CAG GAA GAU GCU CCU CAG ACA CCU AGA CCA
    *** *** ***│*** *** *** *** *** *** *** *** *** *** ***
    AGG UCU CUG│AGC CAG GAA GAU GCU CCU CAG ACA CCU AGA CCA
    Arg Ser Leu│Ser Gln Glu Asp Ala Pro Gln Thr Pro Arg Pro 60                              70
    Glu Thr Ile │Asn Met│Met│Ser│Glu Phe│Val│Ala Asn Leu Pro
    GAA ACC AUA │AAU AUG│AUG│UCA│GAA UUU│GUU│GCU AAU UUG CCA
    *** **  *** │ * *** │***│ * │*** ** │ **│*** *** *** ***
    GAA ACU AUA │AUU AUC│AUG│UUG│GAA UUC│AUU│GCU AAU UUG CCA
    Glu Thr Ile │Ile Ile│Met│Leu│Glu Phe│Ile│Ala Asn Leu Pro
```

FIG. 2A.

```
                                                                    B-chain
                                                              -1 │ 1
      -10
Leu  Leu  Asn  Gln  Phe  Ser  Arg  Ala  Val  Ala │Asp │Ser │Trp
CUA  CUG  AAC  CAA  UUU  UCC  AGA  GCA  GUC  GCG │GAC │UCA │UGG
***  ***  ***  ***  ***  ***  ***  ***  ***  *** │ * *│  * │***
CUA  CUG  AAC  CAA  UUU  UCC  AGA  GCA  GUC  GCG │GCC │AAA │UGG
Leu  Leu  Asn  Gln  Phe  Ser  Arg  Ala  Val  Ala │Ala │Lys │Trp 20
Ala  Gln  Ile  Ala  Ile  Cys  Gly  Met  Ser  Thr  Trp  Ser  Lys
GCG  CAG  AUU  GCC  AUU  UGC  GGC  AUG  AGC  ACC  UGG  AGC  AAA
***  ***  ***  ***  ***  ***  ***  ***  ***  ***  ***  ***  ***
GCG  CAG  AUU  GCC  AUU  UGC  GGC  AUG  AGC  ACC  UGG  AGC  AAA
Ala  Gln  Ile  Ala  Ile  Cys  Gly  Met  Ser  Thr  Trp  Ser  Lys 50
Val  Ala  Glu  Ile  Val  Pro  Ser  Phe  Ile  Asn  Lys  Asp  Thr
GUG  GCA  GAA  AUU  GUG  CCA  UCC  UUC  AUC  AAC  AAA  GAU  ACA
***  ***  ***  ***  **   ***  ***  ***  ***  ***  ***  ***  ***
GUG  GCA  GAA  AUU  GUA  CCA  UCC  UUC  AUC  AAC  AAA  GAU  ACA
Val  Ala  Glu  Ile  Val  Pro  Ser  Phe  Ile  Asn  Lys  Asp  Thr
                     *

80
│Gln │Glu  Leu  Lys │Leu  Thr │Leu  Ser  Glu │Met │Gln  Pro │Ala │
│CAG │GAG  CUG  AAG │UUA  ACC │CUG  UCU  GAG │AUG │CAG  CCA │GCA │
│ *  │***  ***  *** │ *    ** │ **  ***  *** │ * *│ **  *** │ ** │
│CCG │GAG  CUG  AAG │GCA  GCC │CUA  UCU  GAG │AGG │CAA  CCA │UCA │
│Pro │Glu  Leu  Lys │Ala  Ala │Leu  Ser  Glu │Arg │Gln  Pro │Ser │
```

FIG. 2B.

```
                              90
Leu Pro |Gln |Leu Gln Gln |His |Val Pro |Val |Leu Lys Asp Ser
UUA CCA |CAG |CUA CAA CAA |CAU |GUA CCU |GUA |UUA AAA GAU UCC
*** ***  **  *** **  **    **  *** ***  * *  *** **  *** ***
UUA CCA |GAG |CUA CAG CAG |UAU |GUA CCU |GCA |UUA AAG GAU UCC
Leu Pro |Glu |Leu Gln Gln |Tyr |Val Pro |Ala |Leu Lys Asp Ser

120
Arg Gln Ser Glu Ala Ala Asp Ser |Ser |Pro Ser Glu Leu Lys
AGA CAA AGU GAA GCC GCA GAC AGC |AGU |CCU UCA GAA UUA AAA
 ** *** *** *** *** *** *** *** | * *|*** *** *** *** ***
AGG CAA AGU GAA GCC GCA GAC AGC |AAU |CCU UCA GAA UUA AAA
Arg Gln Ser Glu Ala Ala Asp Ser |Asn |Pro Ser Glu Leu Lys 140                                      150
|Leu |Tyr |Ser |Ala Leu |Ala Asn |Lys Cys Cys |His Val |Gly Cys
|CUC |UAC |AGU |GCA UUG |GCU AAU |AAA UGU UGC |CAU GUU |GGU UGU
| * *|*** |    |*** **  | *   *  |*** *** *** | *   ** |*** ***
|CCC |UAC |GUG |GCA CUG |UUU GAG |AAA UGU UGC |CUA AUU |GGU UGU
|Pro |Tyr |Val |Ala Leu |Phe Glu |Lys Cys Cys |Leu Ile |Gly Cys
```

*FIG. 2C.*

```
            100                                                110
 Ser Leu Leu Phe Glu Glu Phe Lys Lys Leu Ile Arg Asn
 AGU CUU CUC UUU GAA GAA UUU AAG AAA CUU AUU CGC AAU
  * * ***  *  *** *** *** *** *** *** *** *** *** ***
 AAU CUU AGC UUU GAA GAA UUU AAG AAA CUU AUU CGC AAU
 Asn Leu Ser Phe Glu Glu Phe Lys Lys Leu Ile Arg Asn
                                                      A-chain
            130                       ┌──────────────┐
 Tyr Leu Gly Leu Asp Thr His Ser  Arg Lys Lys Arg Gln
 UAC UUA GGC UUG GAU ACU CAU UCU  CGA AAA AAG AGA CAA
 *** *** *** *** *** *** *** ***  * * *** *** *** * *
 UAC UUA GGC UUG GAU ACU CAU UCU  CAA AAA AAG AGA CGA
 Tyr Leu Gly Leu Asp Thr His Ser  Gln Lys Lys Arg Arg 160
 Thr Lys Arg Ser Leu Ala  Arg Phe  Cys ***
 ACC AAA AGA UCU CUU GCU  AGA UUU  UGC UGA
 *** *** **  *** *** ***  *  *  *  ***
 ACC AAA AGG UCU CUU GCU  AAA UAU  UGC UGA
 Thr Lys Arg Ser Leu Ala  Lys Tyr  Cys ***
```

*FIG.2D.*

FIG. 5A.

Sequence alignment of insulin and relaxin B-chains and A-chains:

B-chain

| Position | -4 | -3 | -2 | -1 |  | 1 |  |  |  |  |  |  |  |  | 10 |  |  |  |  |  |  |  |  |  |  |  |  |  |  |  |  |
|---|---|---|---|---|---|---|---|---|---|---|---|---|---|---|---|---|---|---|---|---|---|---|---|---|---|---|---|---|---|---|---|---|
| HUMAN INSULIN |  |  |  |  |  | ▼Phe | Val | Asn | Gln | His | Leu | Cys | Gly | Ser | His | Leu | Val | Glu | Ala | Leu | Tyr | Leu | Val | Cys | Gly | Glu | Arg | Gly |  |  |  |
| HUMAN RELAXIN-1 | Ala | ▼Val | Ala | ▼Lys |  | Trp | Lys | Asp | Val | Ile | Lys | Leu | Cys | Gly | Arg | Glu | Leu | Val | Arg | Ala | Gln | Ile | Ala | Ile | Cys | Gly | Met | Ser | Thr | Trp | Ser |  |
| HUMAN RELAXIN-2 | Ala | ▼Val | Ala | ▼Asp |  | Ser | Trp | Met | Glu | Glu | Val | Ile | Lys | Leu | Cys | Gly | Arg | Glu | Leu | Val | Arg | Ala | Gln | Ile | Ala | Ile | Cys | Gly | Met | Ser | Thr | Trp |
| PORCINE RELAXIN |  |  |  |  |  |  |  | Gln | Ser | Thr | Asn | Asp | Phe | Ile | Lys | Ala | Cys | Gly | Arg | Glu | Leu | Val | Arg | Leu | Trp | Val | Glu | Ile | Cys | Gly | Ser |  |
| RAT RELAXIN |  |  |  |  |  | Arg | Val | Ser | Glu | Glu | Trp | Met | Asp | Gln | Val | Ile | Gln | Val | Cys | Gly | Arg | Gly | Tyr | Ala | Arg | Ala | Trp | Ile | Glu | Val | Cys | Gly |
| SHARK RELAXIN |  |  |  |  |  |  |  | Gln | Ser | Leu | Ser | Gln | Glu | Asp | Ala | Pro | Gln | Thr | Pro | Arg | Pro | Val | Ala | Glu | Ile | Val | Pro |  |  |  |  |  |
| DOGFISH RELAXIN |  |  |  |  |  |  |  | Gln | Asn | Ala | Glu | Pro | Gly | Gly | Ser | Ile |  |  |  |  |  |  |  |  |  |  |  |  |  |  |  |  |

A-chain

| Position |  |  | 140 |  |  |  |  |  |  |  | 150 |  |  |  |  |  |  |  |
|---|---|---|---|---|---|---|---|---|---|---|---|---|---|---|---|---|---|---|
| HUMAN INSULIN | Lys | Arg ▼ | Gly | Ile | Val | Glu | Gln | Cys | Cys | Thr | Ser | Ile | Cys | Ser | Leu | Tyr | Gln | Leu | Glu |
| HUMAN RELAXIN-1 | Lys | Lys | Arg ▼ | Pro | Tyr | Val | Ala | Leu | Phe | Glu | Lys | Cys | Cys | Leu | Ile | Gly | Cys | Thr |  |
| HUMAN RELAXIN-2 | Lys | Lys | Arg ▼ | Gln | Leu | Tyr | Ser | Ala | Leu | Ala | Asn | Lys | Cys | Cys | His | Val | Gly | Cys |  |
| PORCINE RELAXIN | Lys | Lys | Arg ▼ | Leu | Phe ▼ | Arg | Met | Thr | Leu | Ser | Glu | Lys | Cys | Cys | Gln | Val | Gly | Cys |  |
| RAT RELAXIN | Lys | Lys | Arg ▼ | Gln | Ser | Gly | Ala | Leu | Leu | Ser | Glu | Gln | Cys | Cys | His | Ile | Gly | Cys |  |
| SHARK RELAXIN |  |  |  | Ala | Thr | Ser | Pro | Ala | Leu | Met | Ser | Lys | Cys | Cys | Ile | Ile | Tyr | Cys |  |
| DOGFISH RELAXIN |  |  |  | Glu | Gly | Ser | Pro | Gly | Met | Ser | Ser | Lys | Cys | Cys | Thr | Tyr | Tyr | Cys |  |

FIG. 5B.

PROCESS FOR SYNTHESIZING HUMAN H2-PRORELAXIN, HUMAN H2-RELAXIN AND FUSION PROTEINS THEREOF

This is a continuation of application Ser. No. 07/665,129, filed Mar. 6, 1991, now U.S. Pat. No. 5,179,195, which is a divisional of application Ser. No. 021,885, filed Mar. 4, 1987, now U.S. Pat. No. 5,023,321, which is a divisional of application Ser. No. 06/560,790, filed Dec. 13, 1983, now U.S. Pat. No. 4,758,516.

This invention relates to the molecular cloning and characterization of a gene sequence coding for human relaxin. The invention is also concerned with recombinant DNA techniques for the preparation of human relaxin, prorelaxin and preprorelaxin.

In our Australian Patent Application No. 17906/83 (PF 5352/82, filed Aug. 12, 1982), we described the molecular cloning and characterization of a gene sequence coding for human relaxin. We have now found a second gene which also codes for human relaxin.

More specifically, this invention relates to an isolated and purified (i.e., "cloned") human gene coding for prorelaxin, preprorelaxin, and the A and/or B and/or C peptide chains of human relaxin, methods for isolating and purifying the genes and a method for transferring the genes to and replicating the genes in a host cell. The cloned genes are expressed by the host cell when fused with a host-expressable prokaryotic or eukaryotic gene. The genes are thus useful in the production of human relaxin for therapeutic purposes.

The invention also relates to the peptides human relaxin, prorelaxin and preprorelaxin, to the individual peptide chains which comprise these sequences and to modified forms of these peptides.

The invention further relates to modified genes coding for the individual relaxin chains and for the above-mentioned modified forms.

[Note: References used in the following description are collected at the end of the description.]

Pioneering work by Hisaw (1926) suggested an important role for the peptide hormone relaxin in mammals through its effects in dilating the pubic symphysis, thus facilitating the birth process. Relaxin is synthesized and stored in the corpora lutea of ovaries during pregnancy and is released into the blood stream prior to parturition. The availability of ovaries has enabled the isolation and amino acid sequence determination of relaxin from pig (James et al, 1977; Schwabe et al, 1977) rat (John et al, 1981) and shark (Schwabe et al, 1982). The biologically active hormone consists of two peptide chains (known as the A and B chains) held together by disulphide bonds, two inter-chain and one intra-chain. The structure thus closely resembles insulin in the disposition of disulphide bonds which has led to speculation of a common ancestral gene for these hormones (James et al, 1977; Schwabe et al, 1977).

Recombinant DNA techniques have been applied to the isolation of cDNA clones for both rat and porcine relaxins (Hudson et al, 1981; Haley et al, 1982), see also Australian Patent Application No. 11834/83 (PF 2696/82). Synthetic undecamer nucleotides, prepared on the basis of amino acid sequence information, were used as primers for the synthesis of cDNA probes greatly enriched in relaxin cDNA sequences which identified relaxin cDNA clones an libraries derived from both rat and porcine ovarian tissue. The relaxin structural gene was found to code in both cases for a single chain precursor which resembles preproinsulin in the overall configuration, i.e., signal peptide/B chain/C peptide/A chain.

In our Application No. 17906/83 we described the use of probes based on the C peptide region of porcine relaxin to select out a relaxin gene from a human genomic library. This approach resulted in the successful identification of a genomic clone which we have now designated "H1" from which the structure of the entire coding region of a human preprorelaxin was determined.

The present invention arises from a continuation of the work described in Application No. 17906/83 in which we sought to confirm the gene structure described in that application. We have investigated cDNA clones in libraries derived from ovarian tissue from pregnant human females using as a probe a segment of the previously identified human H1 gene corresponding to approximately 300 nucleotides of the C peptide/A-chain coding region (amino acids 64–161). Positive cDNA clones were isolated and sequencing of these revealed a cDNA sequence which was not identical with the sequence previously established and which coded for a form of preprorelaxin different to that described in our earlier application.

We have also isolated from the human genomic library described in our copending Australian Patent application No. 17906/83 (PF 5352/82) a recombinant phage containing exon 1 of the H2 gene where exon 1 comprises the coding region of the signal, B-peptide, and part of the C-peptide similar to that of the H1-gene.

It is now believed that either or both the presently-described gene which we have designated "H2" and the "H1" gene described in our Application No. 17906/83 are expressed in human reproductive tissue, for example ovary and placenta, and/or other tissues including but not limited to gut, brain and skin, since both genes express peptides with relaxin-like activity.

The corpora lutea of the ovary as well as decidual and placental tissues are the most likely sites for expression of relaxin-related genes. However, in view of the wide distribution of many peptide hormones it is highly likely that the relaxin gene is also expressed in non-reproductive tissues, including brain and the gastrointestinal tract. Relaxin has the general properties of a growth factor and is capable of altering the nature of connective tissue and influencing smooth muscle contraction. We believe that one or both of the gene structures described in this specification and that of Application No. 17906/83 to be widely distributed in the body. We suggest that the relaxin peptides expressed from these genes will play an important physiological role in addition to their well documented hormonal function during reproduction.

The following abbreviations are used in this description.

H1—the relaxin gene described in Application No. 17906/83, being deduced from a genomic clone.

H2—the relaxin gene described herein, being deduced from a cDNA clone.

| | |
|---|---|
| DNA - deoxyribonucleic acid | A - Adenine |
| RNA - ribonucleic acid | T - Thymine |
| cDNA - complementary DNA (enzymatically synthesized from an mRNA sequence) | G - Guanine |
| | C - Cytosine |
| | U - Uracil |

-continued mRNA - messenger RNA

The coding relationships between nucleotide sequence in DNA and amino acid sequence in protein are collectively known as the genetic code, which is set out below.

| First position (5' end) | Second position | | | | Third position (3' end) |
|---|---|---|---|---|---|
| | U | C | A | G | |
| U | Phe | Ser | Tyr | Cys | U |
| | Phe | Ser | Tyr | Cys | C |
| | Leu | Ser | Stop | Stop | A |
| | Leu | Ser | Stop | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

The abbreviations used for the amino acids in the table are identified as follows.

| Phenylalanine | (Phe) | Histidine | (His) |
|---|---|---|---|
| Leucine | (Leu) | Glutamine | (Gln) |
| Isoleucine | (Ile) | Asparagine | (Asn) |
| Methionine | (Met) | Lysine | (Lys) |
| Valine | (Val) | Aspartic acid | (Asp) |
| Serine | (Ser) | Glutamic acid | (Glu) |
| Proline | (Pro) | Cysteine | (Cys) |
| Threonine | (Thr) | Tryptophan | (Try) |
| Alanine | (Ala) | Arginine | (Arg) |
| Tyrosine | (Tyr) | Glycine | (Gly) |

Each 3-letter codon represented in the table, e.g., AUG, CAU (otherwise known as a nucleotide triplet) corresponds to a trinucleotide of mRNA, having a 5'-end on the left and a 3'-end on the right. The letters stand for the purine or pyrimidine bases forming the nucleotide sequence. All DNA sequences given herein are those of the strand whose sequence corresponds to the mRNA sequence, with thymine (T) substituted for uracil (U).

The invention will be further described and elucidated in the following discussion. Reference will be made to the accompanying drawings in which:

FIG. 1: shows an abbreviated restriction map and sequencing strategy for the cDNA clone in pBR322, genomic clone H11, and GT10 cDNA clones a-f. Arrows indicate the direction of sequencing on end-labelled fragments (see methods). GT10 clones a-f were sequenced by subcloning into an M13 vector as described hereinafter. Nucleotides are numbered from the AUG initiation codon, position 1-3, to the termination codon, position 554-556.

FIGS. 2, 2A, 2B, 2C and 2D: compares the amino acid and mRNA sequence of human preprorelaxin H2 (upper) with the corresponding H1 (lower) sequence. The sequences have been aligned to maximize homology with nucleotide identities being indicated by asterisks and amino acid homologues by boxed-in areas. Amino acids are numbered from the start of the B-chain (H2 gene sequence starting at −1 and H1 sequence at +1) although this position represents only the hypothetical start of the B chain sequence and has been deduced simply from the homology to the related porcine and rat preprorelaxin structures. The asterisk beneath Ala 45 in the C peptide denotes the position of an intron in the G/CA codon in both genes.

Figure 3A:
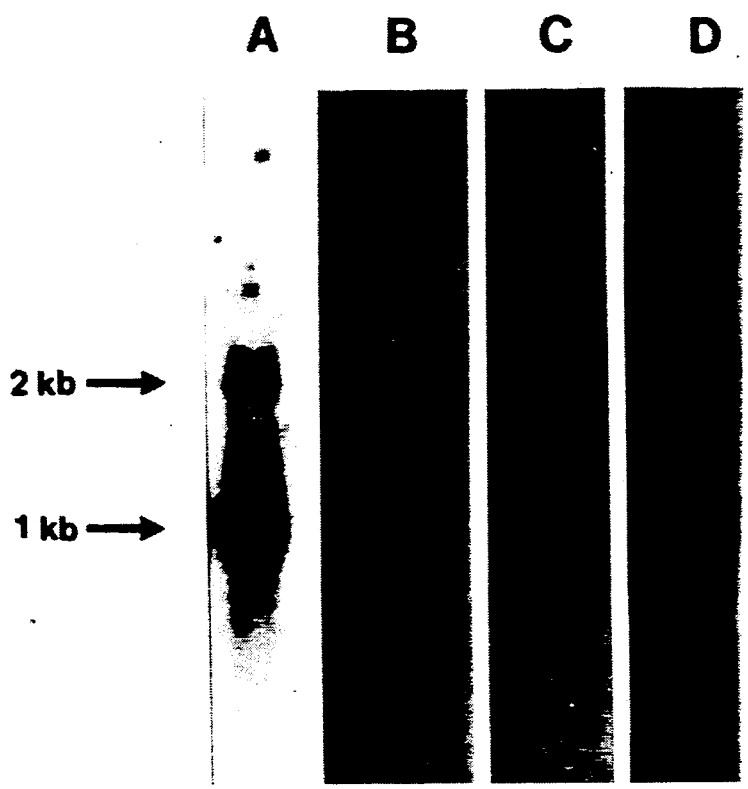
Figure 3B:
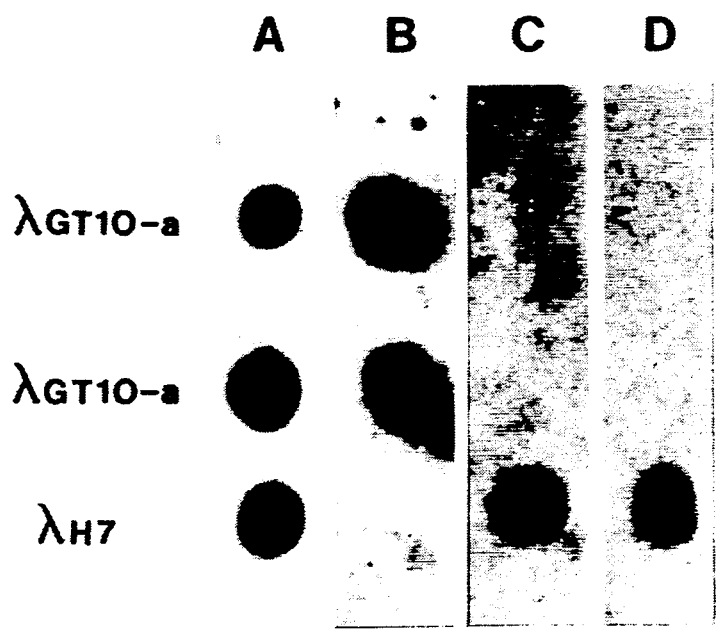

FIGS. 3a and 3b: autoradiographs of identical nitrocellulose strips taken from either a) Northern gel transfer of human ovarian RNA or b) λplaques corresponding to the H1 gene (λH7) or H2 gene (λGT10-a) using as hybridization probes A: a random primed 600 bp H2 relaxin cDNA fragment (72-660), B: H2-specific 25 mer (483-507), C: H1-specific 25 mer (483-507), D: H1-specific 25 mer (248-272).

Figure 4:
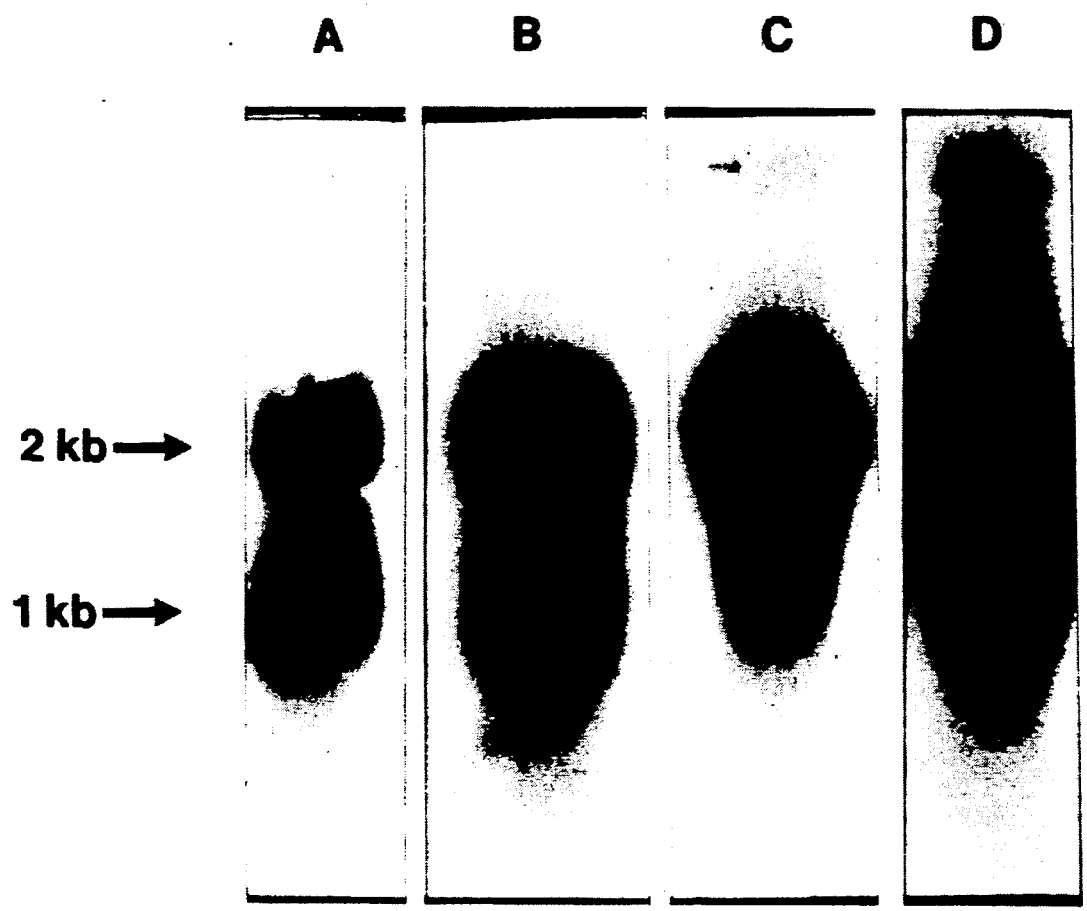

FIG. 4: autoradiographs of identical nitrocellulose strips following Northern gel transfer of human ovarian RNA using as hybridization probes fragments of the H2 cDNA clone in pBR322 (see FIG. 1).

A: 600 bp fragment (72-660) corresponding to most of the coding region

B: 5' untranslated region (to Hinf I site at nucleotide 30)

C: 3' untranslated region (from Hinf I site at nucleotide 660)

D: 3' untranslated region (from Hpa I site at nucleotide 850)

Figure 5:
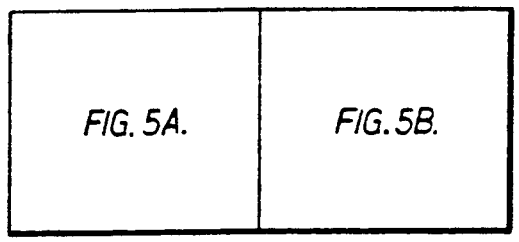
Figure 5B:
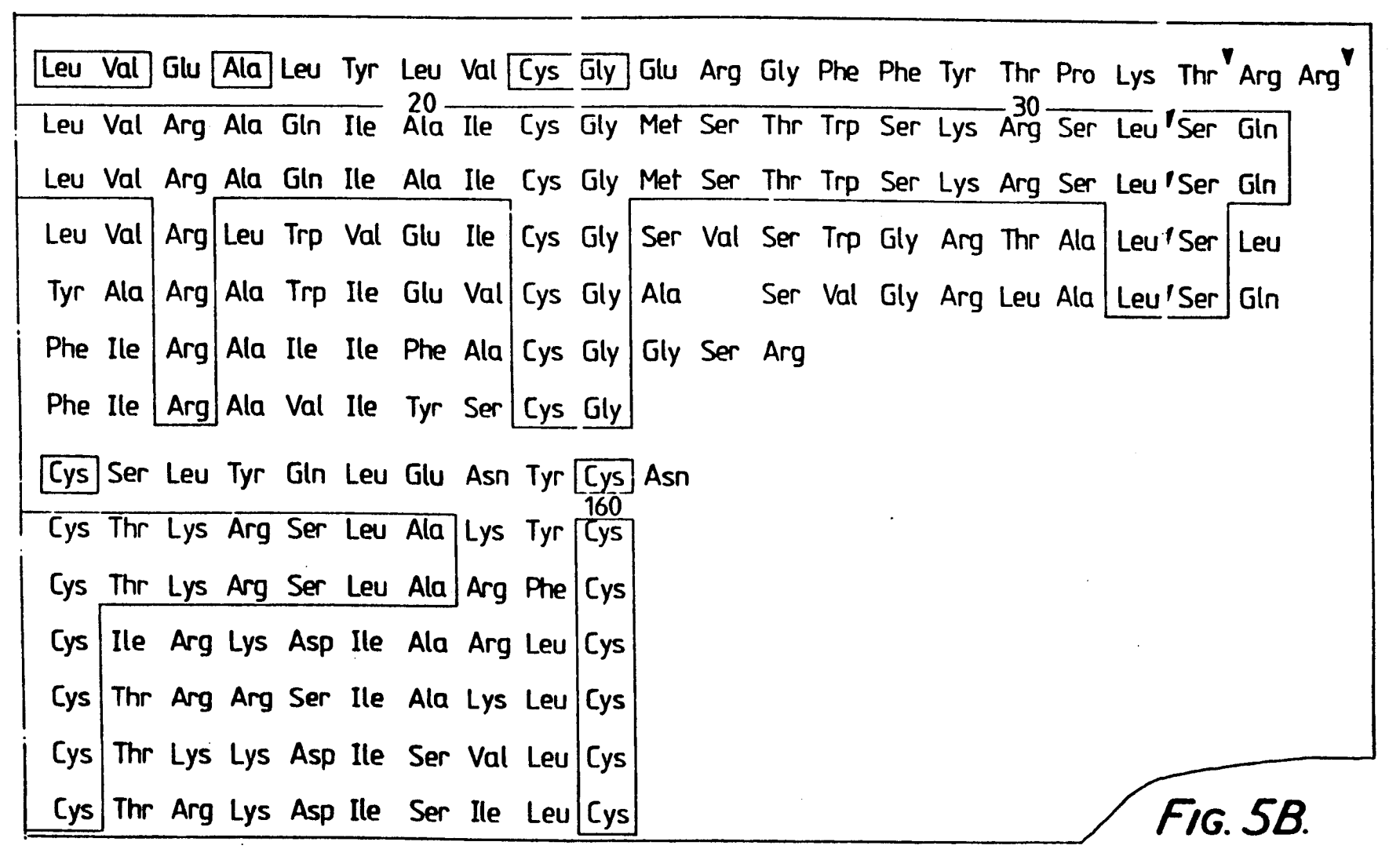

FIGS. 5, 5A and 5B: comparison of the amino acid sequences of the B and A chains between the two human relaxin genes, human insulin, and other members of the relaxin family. Boxed areas highlight residue which are conserved between the two human relaxin genes and the relaxin family. Arrows indicate probable sites of proteolytic cleavage with confirmation by protein sequencing data of the amino terminal residue of the B and A chains of porcine (Schwabe et al, 1977; James et al, 1977), rat (John et al, 1981), shark (Schwabe et al, 1982) and dogfish relaxins (Schwabe et al, 1982).

The H2 mRNA sequence shown in FIG. 2 was determined by the methods described hereinafter. For ease of comparison, the numbering of the amino acids previously used for the peptide derived from the H1 sequence has been maintained in the present description of the H2-derived peptide. The structure of H1-preprorelaxin was deduced from the genomic sequence by comparison with the homologous structures of pig and rat relaxin. The H2-preprorelaxin structure was deduced by comparison with the H1 structure as well as the pig and rat structures. Confirmation of the A and B peptide chain structures has been provided by synthesis and chain recombination in vitro which produces a material which is biologically active in the uterine contraction assay.

Figure 2:
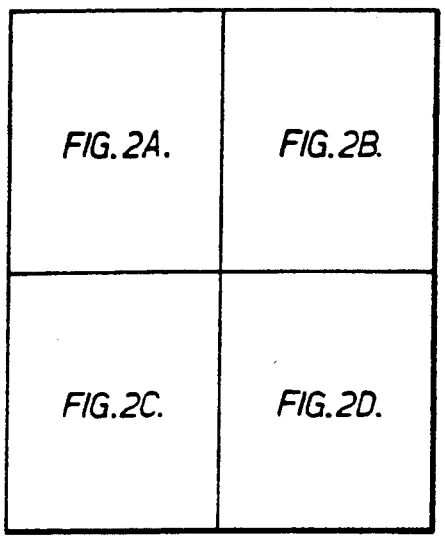

It will be seen from FIG. 2 that the present and previous sequences show significant differences as well as similarities. Notable are:

(1) Significant amino acid differences in three main areas:
   (a) the N-terminus of the B-chain
   (b) the N-terminus of the A-chain
   (c) the middle of the C-peptide.

(2) Regions of strong homology in the B-chain, and C-peptide:
   (a) 120 identical bases from $Val^6$ to $Ile^{47}$.
   (b) 88-90 identical bases from $Phe^{101}$ to $Ser^{132}$.

The two genes are therefore very similar but the differences are sufficient to indicate that the H2- gene is indeed a second gene and not simply a polymorph of H1.

The mode of in vitro processing of the H1 preprorelaxin is not yet fully known but by analogy with pig relaxin, cleavage of the signal peptide would be expected to occur at the $Ala^{-1}$-$Lys^1$ bond. Similarly excision of the H1-C peptide is predicted to occur at $Leu^{32}$-$Ser^{33}$ and $Arg^{136}$-$Arg^{137}$, thus giving the H1-B and H1-A chains of respectively 32 and 24 residues (FIG. 2).

In H2 preprorelaxin $Ala^{-1}$ has been replaced by Asp and so we would predict cleavage of the signal peptide after the alanine corresponding to position $-2$ in H1. Cleavage at the H2-B chain/C peptide junction is expected after $Leu^{32}$ by anlogy to all other prorelaxins, thus leaving the H2-B chain with 33 residues. Cleavage at the H2-C peptide/A chain junction would occur after $Arg^{136}$ by analogy to rat preprorelaxin, thus leaving the H2-A chain with 24 residues.

As noted in our studies on pig relaxin, there are core sequences in the pig relaxin B and A chains which contain all the essential elements for biological activity. Our synthetic studies on the human relaxin chain show similar results, as set out in more detail hereinafter.

According to one aspect of the present invention, there is provided a gene for the expression of human H2-preprorelaxin.

Except where otherwise specified, all following references to the gene sequences for preprorelaxin, prorelaxin, relaxin and the signal, A, B and C peptides, and to the peptides themselves will be understood to refer to the H2 varients and to exclude the H1 variants.

More specifically, this aspect of the invention provides a double-stranded DNA fragment for the expression of human preprorelaxin, which comprises a coding strand and a complementary strand corresponding to the complete mRNA (condons $-25$ to 160) sequence shown in FIG. 2 of the accompanying drawings.

The invention also includes any sub-unit of the H2-preprorelaxin gene sequence described herein, or any equivalent of the said sequence or sub-unit. Among the sub-units to be included by this statement are the individual structural genes coding for the signal peptide chain and the separate H2-A and H2-B peptides and the H2-C chain of human preprorelaxin (see FIG. 2) and any combinations of these chains, e.g., the genes for expressing the H2-A and H2-B peptides, separately or as prorelaxin (with the H2-C chain). The sub-units also include fragments and combinations of fragments of any of said gene sequences.

Thus according to another aspect of the present invention, there is provided a gene for the expression of human prorelaxin.

More specifically, this aspect of the invention provides a double-stranded DNA fragment for the expression of human prorelaxin, which comprises a coding strand and a complementary strand corresponding to the codons numbered as 1 to 160 of the mRNA sequence shown in FIG. 2 of the accompanying drawings.

According to a further aspect of the present invention, there are provided genes for the separate expression of the A, B and C chains of human relaxin or any combination of two or more of the said chains and any fragment or combination of fragments of the said chains.

More specifically, this aspect of the invention provides double-stranded DNA fragments for the separate expression of the A and/or B and/or C chains of human relaxin (or fragments as described above) which comprise a coding strand and a complementary strand corresponding to the codons numbered $-1$ to 32, 33 to 136 and 137 to 160 of the mRNA sequence shown in FIG. 2 of the accompanying drawings.

The genes described above in addition to the codons specified may also include the appropriate "start" and "stop" codons, e.g., AUG and UGA respectively (codons $-25$ and 161 in FIG. 2).

Those skilled in the art will appreciate that polymorphic forms of the genes may exist. Such forms are included in the present invention.

The invention further includes the complements of the above sequences, sub-units or equivalents, and the corresponding RNA sequences, sub-units or equivalents.

According to another aspect of the present invention there is provided a DNA transfer vector comprising the deoxynucleotide sequences corresponding to the genes defined above.

As shown above, the genetic code contains redundancies, that is certain amino acids are coded for by more than one codon. Thus the invention includes deoxynucleotide sequences in which the codons depicted in the drawings, or their cDNA equivalents are replaced by other codons which code for the same amino-acid.

Furthermore, as already indicated above, peptides with relaxin activity may be produced which differ from the B and/or A chain structures of natural relaxin. Such differences may involve deletion of one or more amino acids and/or addition of further amino acids and/or substitution of different amino acids in the natural chains.

Thus the invention also includes genes and DNA transfer vectors as described above wherein one or more of the natural codons are deleted and/or are replaced by codons which code for amino acids other than that coded by the natural codon, and/or further codons are added to the natural sequence.

The transfer vectors of the invention may also include inter alia, genetic information which ensures their replication when transferred to a host cell. Such cells may include, for example, the cells of prokaryotic microorganisms, such as bacteria, yeasts and moulds, and also eukaryotic cells, including mammalian cells and cell lines.

Examples of transfer vectors commonly used in bacterial genetics are plasmids and the DNA of certain bacteriophages. Both phage DNA and bacterial plasmids have been used as the transfer vectors in the present work. It will be understood however, that other types of transfer vectors may be employed. The general techniques of forming such transfer vectors and transforming them into microorganisms are well known in the art.

The invention also includes a prokaryotic or eukaryotic cell transformed by any of the transfer vectors described above.

One preferred microorganism is the very familiar *Escherichia coli*, but any other suitable microorganism may be used.

According to a still further aspect of the present invention, there is provided a process for making a DNA transfer vector for use in maintaining and replicating a deoxynucleotide sequence coding for human preprorelaxin, characterised by ligating a deoxynucleotide sequence coding for human preprorelaxin with a DNA molcule prepared by cleaving a transfer vector with a restriction enzyme.

DNA transfer vectors for use in maintaining and replicating deoxynucleotide sequences coding for human prorelaxin and for the A and B chains of human relaxin may be similarly prepared from the appropriate deoxynucleotides.

The A and B peptide chains, and also prorelaxin and preprorelaxin may be prepared by the usual process of gene expression, that is by growing cells containing the appropriate transformed transfer vector and isolating and purifying the required peptide(s) produced by the cells.

Thus, the invention further includes a process for making a fusion protein comprising the amino acid sequence of human preprorelaxin as its C-terminal sequence and a portion of a prokaryotic or eukaryotic protein as its N-terminal sequence, characterised by incubating a cell culture transformed by an expression transfer vector comprising a deoxynucleotide sequence coding for human preprorelaxin, prepared in accordance with the process described above.

Fusion proteins comprising the amino acid sequences for human prorelaxin and/or the A and/or B and/or C chains of human relaxin may be similarly prepared.

The fusion peptide products thus produced will be in the form of a fusion protein in which the desired peptide is linked with a portion of a prokaryotic or eukaryotic protein characteristic of the host cell. Such fusion proteins also form a part of this invention.

The invention also includes a process for synthesizing human prorelaxin comprising the A and B peptides separated from each other by a C peptide, characterised by incubating a culture of cells, transformed by an expression transfer vector comprising a deoxynucleotide sequence coding for said human prorelaxin, prepared as described above, under conditions suitable for expression of said sequence coding for human prorelaxin, and purifying human prorelaxin from the lysate or culture medium of said cells.

The peptide of interest can be recovered from the fusion product by any suitable known cleavage procedure.

As already indicated above the transfer vector may be modified by codon substitution/deletion/addition and such modifications will give rise to modified fusion peptides. In this way appropriate modifications may be made to facilitate the cleavage of the fusion peptides, for example, at the junction of B/C or C/A chains or to modify the peptide chain behaviour during subsequent chemical or biological processing.

As indicated above, the invention also provides human relaxin, prorelaxin and preprorelaxin.

Relaxin may be prepared by direct combination of the separate A and B chains by any of the procedures currently known and used for the preparation of insulin.

Also in a similar manner to insulin, relaxin may be prepared from prorelaxin by oxidizing or otherwise converting the sulfhydryl groups on the A and B peptides of relaxin, prepared as described herein, to form disulfide crosslinks between said A and B peptides, and then excising the C peptides, for example, by an enzyme-catalyzed hydrolysis specific for the bonds joining the C peptide to the A and B peptides.

Accordingly, the present invention further provides a method for the synthesis of human relaxin which comprises combining the A and B chains of relaxin (in their full-length, shortened or modified forms) by methods known per se for combination of A and B chains of human insulin.

One such method comprises reducing a mixture of the S-sulphonated A and B chains and then allowing the mixture to oxidize in air.

We have also found that the efficiency of the above procedure is improved when one or both of the A and B chains is in the form of an S-thioethyl-cys derivative rather than the S-sulpho form.

In our Australian Patent Application No. 15413/83 (PF 4385/82) we also showed that one or both of the A and B chains of relaxin can be shortened at the amino and/or carboxy terminii without significant loss of biological activity and with improved combination yields. These techniques apply equally to the preparation of human relaxin.

Another aspect of the invention provides a human relaxin analogue consisting essentially of shortened and/or modified forms of the natural B and/or A peptide chains.

This aspect of the invention also provides a method or producing a human relaxin analogue which comprises the step of forming the shortened and/or modified B and/or A peptide chains and combining them by any of the methods described above.

Our investigations with both pig and human relaxin (H1) show that relaxin activity may be present with human A chains as short as A(10–24) and B chains as short as B(10–22) although the expected practical minima are respectively A(4–24) and B(4–23). The synthetic pig peptide A(4–24)-B(1–25) is already known to have relaxin activity.

In general, for the present relaxin structure (H2) the A chain can be varied from A(1–24) to A(10–24) and B chain from B(−1–32) to B(10–22).

The preferred combinations are derived from:

|        | A                            |              | B                              |
|--------|------------------------------|--------------|--------------------------------|
| any of | (1–24)<br>(2–24)<br>(3–24)   | with any of  | (−1–23)<br>(up to)<br>(−1–32)  |

Modifications of the B and/or A chains, in accordance with the present invention may involve either "genetic" modification, as described above, or chemical modification of the B and/or A chains (in either full-length or shortened form) prior to combination by the method of the invention. Two types of modification may be employed, either singly or in combination.

The first type involves the modification of one or more of the amino-acids which occur in the natural or shortened B and/or A chains. Such modification will generally involve protection of active groups on one or more of the amino-acids by methods known per se, and the protecting groups may, if desired, be removed after combination of the (modified) A and B chains.

Examples of this type of modification include the acetylation, formylation or similar protection of free amino groups, including the N-terminal, amidation of C-terminal groups, or the formation of esters of hydroxyl or carboxylic groups. The formyl group is a typical example of a readily-removable protecting group.

The second type of modification includes replacement of one or more of the natural amino-acids in the B and/or A chains with a different amino acid (including the D-form of a natural amino-acid). This general type of modification may also involve the deletion of a natural amino-acid from the chain or the addition of one or more extra amino-acids to the chain.

The purpose of such modifications is to enhance the combination yields of the A and B chains, while maintaining the activity of the product, i.e., relaxin or an analogue thereof, or to enhance or modify the activity of the product for a given combination yield. Such modification may extend to the production of synthetic analogues which have relaxin-blocking or -antagonistic effects.

A specific example of the first type of modification is the modification of the tryptophan (Trp) residue at B2 by addition of a formyl group.

Examples of the second type of modification are replacement of the Met moiety at B24 with norleucine (Nle), valine (Val), alanine (Ala), glycine (Gly), serine (Ser) or homoserine (HomoSer).

The invention in this aspect also includes human relaxin analogues formed from natural or shortened B and/or A chains modified in accordance with the invention as described above.

The A and B peptide chains, and also prorelaxin and preprorelaxin may be prepared by the usual process of gene expression, that is by growing a microorganism containing the appropriate transformed transfer vector and isolating and purifying the required peptide(s) produced by the microorganism.

The peptide products thus produced may be in the form of a fusion protein in which the desired peptide is linked with a portion of prokaryotic protein The invention is further described and illustrated by the following description of the experimental procedures used and the results obtained thereby.

METHODS AND MATERIALS

Messenger RNA Isolation and cDNA Cloning

Human ovarian tissue obtained during surgery for the treatment of an ectopic pregnancy was quickly frozen on dry ice and the RNA isolated in 5M guanidinium thiocyanate (Merck) according to the method of Chirgwin et al., 1979. Poly-A+ RNA was converted into double stranded DNA (Wickers et al, 1978) and cloned either by the homopolymeric G/C tailing method into a pBR322 plasmid vector (Chang et al., 1978) or by the lambda packaging method using the λGT10 vector (Huynh et al., 1983). In our experience the efficiency of transformation with the pBR322 method ($10^4$ recombinants/μg of cDNA) was far less efficient than the lambda technique (up to $10^6$ recombinants/μg of cDNA).

Preparation of Hybridization Probes

Radiolabelled probes were prepared by primed synthesis on various DNA fragments using denatured random primers of calf thymus DNA (Hudson et al., 1983, Taylor et al., 1976). The DNA template (100–200 ng) was denatured with the random primers (1 μg) by boiling in 20 μl of water for 2 minutes. Synthesis was initiated by the addition of a 30 μl reaction mixture containing 50 mM Tris-HCl pH 8.0, 50 mM NaCl 1 mM DTT, 10mM MgCl$_2$, 5 units of E. coli DNA Polymerase 1 (Klenow fragment), 500 μM each of dCTP, dGTP, dTTP and 0.3 μM α-[$^{32}$P]-dATP (Approx. 3000 Ci/mmol, Amersham). After incubation at 37° C. for 30 minutes the reaction was terminated by dilution into 300 μl of a buffer containing 0.3M NaCl, 10 mM Tris-HCl, pH 8.0, 1 mM EDTA and passed through a Sephadex-G50 column, (1 cm×5 cm) in the same buffer. The radiolabelled probe was collected from the peak fractions at void volume and precipitated with 2 volumes of ethanol at −20° C. for 2 hours using tRNA (10 μg) as carrier.

Selection of Specific cDNA Clones

To screen the human ovarian cDNA clone bank for relaxin specific sequences we used as a probe a segment of the previously identified human H1 gene corresponding to a 400 nucleotide segment coding for the C peptide and A-chain from amino acid 64, through the termination codon and including 80 bases of the 3' untranslated region. A single positive cDNA clone from the pBR322 library was isolated and sequenced. 23 unique recombinants were isolated from the λGT10 libraries, but of these only 6 were subjected to complete nucleotide sequence analysis.

DNA Sequence Analysis

The sequencing strategy and an abbreviated restriction map of the cDNA clones are summarized in FIG. 1. The recombinant plasmid in pBR322 was digested with restriction enzymes Hpa II (P), Hinf I (F) or Taq I (T) and end-labelled using reverse transcriptase and the appropriate α-labelled deoxynucleotide triphosphate (dCTP for Hpa II, and Taq I, dATP for Hinf I). Fragments were cleaved internally with a second restriction endonuclease and then separated by electrophoresis on 8% polyacrylamide gels prior to sequencing by the chemical degradation method of Maxam and Gilbert et al, 1977.

cDNA clones in λGT10 were sequenced by subcloning Eco R1 restriction fragments into M13mp9 and employing the techniques described by Sanger et al, (1980).

Southern and Northern Gel Analyses

Performed on purified genomic DNA after restriction endonuclease cleavage by the method of Southern (1975) or on purified RNA. The DNA fragments which were used as probes were found to be specific for either exon I or exon II of the H1 genomic clone despite having a small amount of flanking sequences. These fragments were generated by subcloning into M13mp8 a 500 bp Alu I fragment of the λH7 clone in the case of the exon I probe, or a 400bp Eco RI-Ava II fragment for the exon II probe. A probe from the H2 cDNA clone was generated by digesting with Hinf I and isolating a 300 bp doublet corresponding to the coding region from Asp 1 to the termination codon and including 110 bases of the 3' untranslated region (FIG. 1). Oligonucleotide probes were synthesized by the phosphite chemistry method of Beaucage and Caruthers (1981) and were end-labelled with γ-$^{32}$P-ATP using T4 polynucleotide kinase. Hybridization conditions were calculated on the basis of the G+C content.

Isolation and Nucleotide Sequence Analysis of the H2 Genomic Clone

The human genomic lambda library of Lawn et al (1978) was screened by method described earlier (Hudson et al, 1983) except that a mixture of DNA fragments corresponding to exons I and II of the H1 genomic clone was used for the probe as described above. Positive phage were grown in liter scale liquid cultures, the DNA isolated and digested with restriction endonucleases prior to mapping with the exon I and II probes.

A 4 kilobase EcoR1 fragment was found to contain the entire exon I coding region which differentiated this clone from the homologous H1 gene structure. This fragment was subcloned into M13mp8 and sequenced by the technique of Maxam and Gilbert (1977). After digesting with Ava I, fragments spanning the coding region were end-labelled and cleaved internally by a second restriction enzyme (Hpa II of Hinf I) to generate fragments suitable for sequence analysis.

Isolation of a cDNA Clone

Samples of human corpus luteum were made available to us as a result of surgical intervention in ectopic pregnancies or from lutectomy at the time of Caesarian section. From the RNA isolated from a single corpus luteum a cDNA library was constructed in pBR322 providing about 300 unique recombinants. Screening this library with an H1-cDNA probe revealed a single recombinant with sequence homology to human relaxin I. To increase the total number of recombinants from such small amounts of ovarian tissue we constructed cDNA libraries using the λGT10 cloning system (Huynh et al, 1983). Screening with a relaxin-specific probe identified 23 unique cDNA clones of which six were characterized as shown in FIG. 1. Nucleotide sequence analysis revealed that all 6 cDNA recombinants encoded fragments of the same relaxin structural gene (FIG. 2), yet this sequence was different to the genomic clone reported earlier (Hudson et al., 1983). We expected that this novel sequence corresponded to the second human relaxin gene (H2) which had been observed in genomic DNA.

Surprisingly, none of the cDNA clones contained a polyadenosine sequence at the 3' end, although the size of cDNA clones in PBR322 and λGT10 (1800 bp and 1900 bp respectively) indicate that large transcription products were being synthesized during the cloning procedure. These two cDNA clones had overlapping sequence identity at the 3' terminus confirming that they were derived from the same mRNA structure. We attributed the loss of the poly-A tail either to premature termination of the double-stranding transcription reaction or to excessive S1 nuclease degradation during the cloning procedure.

Isolation of a Genomic Clone Corresponding to the Second Gene

A thorough screen of $10^8$ recombinant phage from the human genomic library of Lawn et. al., (1978) using mixed probes specific for exon I or II of the λH7 relaxin clone revealed 16 positive phage. Small scale restriction mapping analysis revealed that 14 of these recombinant phage corresponded to the H1 relaxin gene reported earlier (11 were identical to the λH7 genomic clone; 3 were identical to λH5 a different genomic clone of the H1 gene as previously reported by Hudson et. al., 1983). However, the other 2 recombinant phage were identical and had a unique restriction pattern characteristic of the H2 relaxin gene whose structure is given in FIG. 1. The unusual ratio of recombinants reflects either their proportion in the original genomic library or results from selective growth during amplification. Southern blot analyses of this new recombinant phage (λH11) using separate probes corresponding to either exon I or II of the λH7 clone, revealed that λH11 contained only the exon I coding region. Attempts to find a full length genomic clone corresponding to the H2 relaxin gene either in the library of Lawn et. al. (1978) or in another library (Dr. R. Crawford, unpublished) have so far been unsuccessful.

The nucleotide sequence of the relaxin coding region of λH11 was found to be identical to that observed in the cDNA clone shown in FIG. 2. An intron interrupts the coding region in exactly the same position as in the λH7 genomic clone (Hudson et. al., 1983) suggesting that these genes arose by a gene duplication event at some point in evolution.

Northern Gel Analysis

RNA was isolated from several samples of human corpora lutea taken from different individuals during surgical intervention for ectopic pregnancy or during Caesarian section operations. Northern gel analysis using probes made from the coding region of either relaxin gene revealed that two major mRNA species of approximate sizes 1000 bp and 2000 bp were present in five human ovarian RNA samples tested (FIG. 3). The smaller mRNA species were 2-3 fold more abundant in the RNA samples tested and this result was independent of whether the probe used in the analysis corresponded to H1 or H2 relaxin indicating that high cross-hybridization rates occur under our experimental conditions. To differentiate whether these two mRNA species represent the separate products of the H1 and H2 genes, oligonucleotide probes were synthesized over a region of minimum homology (60%) between the two relaxin genes (residues 137-144 in FIG. 2). These synthetic 25 mers were radiolabelled by kinasing with $\gamma$-$^{32}$P-ATP and used as hybridization probes under conditions shown to provide specificity for either the H1 or H2 gene (FIG. 3). Northern gel analysis using these radiolabelled probes revealed that both mRNA species corresponded to products of the H2 gene. We could not detect any transcription products from the H1 gene using the specific probes, although low level expression (less than 5% of the H2 level) would have been difficult to identify.

To analyse the different mRNA transcripts from the H2 gene, we made specific probes from segments of the two large H2 cDNA clones corresponding to the coding region and 5' and 3' untranslated regions (FIG. 4). The larger mRNA transcript (approximately 2 kb in length) selectively hybridized to segments of the 3' untranslated region from both cDNA clones, from a position approximately 100 bases from the termination codon. A potential polyadenylation signal exists in the nucleotide sequence of the cDNA clones, 140 bases from the termination codon, and this region does have homology to the porcine relaxin polyadenylation site. However, the question of whether the shorter mRNA product is polyadenylated near this position cannot be resolved until full length cDNA clones corresponding to both mRNA forms have been isolated and characterised.

In the absence of the genomic sequence of the H2 gene it is impossible to define the mechanisms leading to the formation of the two mRNA transcripts. It is possible, like the collagen and $\beta$-microglobulin genes, that cleavage of the primary RNA transcript could occur at alternative polyadenylation sites. On the other hand we cannot rule out the possibility of alternative splicing mechanisms such as occurs in the calcitonin, growth hormone and $\alpha$-crystallin genes.

The Primary Structure of Preprorelaxin Encoded by the H2 Gene

The mode of in vivo processing of the human preprorelaxin genes is not yet fully understood and has to be deduced by analogy to the processing of porcine and rat preprorelaxins (FIG. 5). The predicted B and A chain structures for the H1 and H2 genes have been aligned to other members of the relaxin family and human insulin in FIG. 5.

Cleavage of the signal peptide in H1 has been predicted (Hudson et al., 1983) to occur after a short side chain residue such as Ala$^{-1}$, -2 or -4 or after Ser-6. Cleavage after Ala-1 is consistent with the homology to porcine preprorelaxin and human preproinsulin. Similarly, cleavage of the H2 signal peptide probably occurs after Ala-2 by such analogy, although cleavage after Ala-4 or Ser-6 are other possibilities.

By analogy to rat and pig prorelaxins, cleavage at the B chain/C peptide junction would occur after Leu 32 in both H1 and H2 precursors. However, both human relaxin B chains possess at positions 29-30 the conserved dibasic sequence Lys-Arg, which is a known processing site in other prohormones such as proinsulin, and cleavage here cannot be excluded. Direct amino acid sequence analysis of relaxin isolated from corpora lutea of pregnancy will be required to settle this point. In the meantime it seems that the most likely structure of the H1 B chain would be 32 residues in length (Lys 1 to Leu 32) and the H2 B chain would be 33 residues (Asp-1 to Leu 32).

Cleavage at the C peptide/A chain junction of H1 prorelaxin has been predicted (Hudson et al., 1983) to occur after Arg 136 within a group of 4 basic residues because the Arg-Pro imide bond at 137-138 would be resistant to proteolysis. H2 prorelaxin has the same sequence of 4 basic residues and a similar processing step after Arg 136 would result in both the H1 and H2 relaxin A chains being 24 residues in length.

Biological Activity of the H2 Gene

As noted in earlier studies on synthetic pig relaxin peptides, there are core sequences in the pig relaxin B and A chains which contain all the essential elements for biological activity. Our synthetic studies on the H1 relaxin peptides has shown that combination of the complete H1 A chain (Arg 137-CYS 160) to a shortened form the H1 B chain (Lys 1-Ser 25) produced material which possessed biological activity (Hudson et al., 1983). Further studies on both the H1 and H2 gene structures using peptide synthesis reveals that both genes code for forms of relaxin which are biologically active in the rat uterine contractility assay.

Chemical Synthesis of a Modified Human Relaxin H2 (hRLX) A(1-24)-B(−1-24)

(i) Synthesis of human relaxin A-chain, H2 hRLX A(-1-24)

The amino acid sequence corresponding to residues 1 to 24 of the human relaxin A-chain, deduced as described above from the nucleotide sequence of the cDNA clone, was synthesized by the solid-phase procedure according to the general principles described by Merrifield (e.g. Barany, G. and Merrifield, R. B. In "The Peptides". Ed. E. Gross & J. Meienhofer, Academic Press, New York, pp. 1-284, 1980).

N-α-tertiarybutyloxycarbonyl* -4-methylbenzyl-L-cysteine (*hereinafter "BOC") was coupled to a 1% crosslinked polystyrene resin via the phenylacetamidomethyl (PAM) linkage to a level of 0.30 mmole/gm using the method of Tam et al., (Synthesis 12, 955-957, 1979). The BOC-L-CYS-PAM resin (8.0 gm) was transferred to the reaction vessel of a Beckman Model 990 Peptide Synthesizer and the amino acid sequence from residues 23 through to 1 was assembled by the stepwise addition of each suitably protected amino acid. The amino terminal BOC protecting group of each amino acid was removed by treatment of the resin with 35% trifluoroacetic acid in methylene chloride for 30 minutes followed by neutralization with 5% diisopropylethylamine in methylene chloride for 15 minutes. After each treatment the resin was washed thoroughly with methylene chloride. The next amino acid in the sequence (suitably protected at the α-amino with the BOC group and where necessary with the 7 side-chain functional group appropriately protected) was coupled to the resin using dicyclohexylcarbodiimide (DCC). The resin was stirred with the amino acid in methylene chloride for 10 minutes prior to the introduction of the DCC which was also dissolved in methylene chloride. A 2.5 molar excess (6.0 mmole) of amino acid and DCC was used for each coupling. After stirring for 1 hour a sample of the resin was removed from the reaction mixture and tested for the presence of free amino groups using the ninhydrin procedure of Kaiser et al. (Anal. Biochem., 34, 595-598, 1970). If the ninhydrin test was negative indicating complete coupling the reaction cycle was continued with BOC deprotection, neutralization and coupling of the next amino acid. For a positive ninhydrin test the coupling reaction was repeated with further amino acid and DCC.

Amino acids with side-chain functional groups were used as the following protected derivatives: N-α-BOC-2,6-dichlorobenzyl-L-tyrosine, N-α-BOC-ξ-chlorobenzyloxycarbonyl-L-lysine; N-α-BOC-L-serine O-benzyl ether; N-α-amyloxycarbonyl-N$^G$-tosyl-L-arginine; N-α-BOC-L-threonine O-benzyl ether; N-α-BOC-S-ethyl mercapto-L-cysteine (for CYS at A-chain sequence position 15, 11 and 10).

Following the assembly of the 1-24 peptide sequence, the final BOC group on the amino terminal arginine was removed using the deprotection neutralization cycle and the peptide-resin dried in vacuo (wt of peptide resin 13.0 gm). A portion of the peptide-resin (2 gm) was treated with anhydrous hydrogen fluoride in the presence of anisole (2 ml) at 0° C. for 30 minutes. The total time for contact of the resin-peptide with hydrogen fluoride (HF) was kept to a minimum (not more than 70 minutes) by rapid removal of the HF under oil-pump vacuum. The resin-peptide was then washed several times with ethyl acetate to remove excess anisole, the peptide extracted into 1M acetic acid and the solution lyophilized. The yield of crude peptide, (with the cysteines at positions 10, 11 and 15 still protected as the S-thioethyl derivative) was 392 mg. Initial purification of the crude peptide was by gel-filtration on Biogel P10 in 0.1M acetic acid. The fractions representing the major peak from this column, which eluted at a position corresponding to a molecular weight of approximately 3000, were collected and lyophilized. Amino acid analysis of a sample of this peptide indicated that all the amino acids of the 1-24 sequence were present in the correct ratio.

Further purification of the [S-thioethyl Cys$^{10,11,15}$]-hRLX A(1-24) peptide was effected by preparative reverse-phase HPLC on a Waters C-18 Bondapak column using a 0.1% TFA-water/acetonitrile solvent system.

A sample (80 mg) of the peptide purified by gel-filtration was S-sulfonated with a mixture of sodium sulfite and sodium tetrathionate (total reaction time of 3 hours) according to the method described by Du et al., (Scientia Sinica, 10I, 84–104 (1961)). The precipitate which formed during the S-sulfonation reaction was removed by filtration and both the precipitate and the supernatant solution dialyzed against distilled water at 4° C. for 48 hours. The contents of the dialysis bags were lyophilized to yield 39.5 mg of peptide from the supernatant solution and 20.3 mg of peptide from the precipitate which occurred during the S-sulfonation reaction. A sample of the 'soluble' [S-sulfo $Cys^{10,11,15,24}$] hRLX A(1-24) peptide was purified by preparative reverse-phase HPLC on a Waters C-18 Bondapak column using a 0.1% TFA-water/acetonitrile solvent system.

(ii) Synthesis of shortened human relaxin B-chain, H2 hRLX B (−1-24)

The amino acid sequence corresponding to residues −1 to 24 of the H2 human relaxin B-chain was synthesized using the procedures described above and commencing with 6.0 gm N-α-tertiarybutyloxycarbonyl-L-methionine-phenylacetamido-methyl polystyrene resin with a loading of 0.5 mmole Met per gm. The side-chain protecting groups used in the A-chain synthesis were also employed for the B-chain including the S-ethyl mercapto derivative for both cysteines at positions 10 and 22. The glutamic acid residues at positions 4 and 5 and the aspartic acid residue at −1 were added as the N-α-BOC-benzyl ester derivative. The glutamine at position 18 was coupled by the active ester procedure using N-α-BOC-L-glutamine-p-nitrophenyl ester in DMF. Following coupling of the tryptophan at position 2, 0.1% indole was added to the trifluoroacetic acid deprotecting reagent and to the subsequent methylene chloride washes.

The final weight of peptide-resin after removal of the BOC group from the amino terminal aspartic acid residue and vacuum-drying was 8.5 gm. A portion of the peptide resin (3.5 gm) was treated with anhydrous hydrogen fluoride in the presence of anisole (2 ml) at 0° C. for 30 minutes and the B-chain peptide isolated using the procedure described above for the A-chain. The crude [S-thioethyl $Cys^{10,22}$] hRLX B(−1-24) (0.97 gm) was purified by gel filtration on BioGel P10 in 1M acetic acid followed by preparative HPLC.

A sample (100 mg) of the peptide purified by gel filtration was S-sulfonated at pH 8.3 for 3 hours, the reaction mixture filtered and the precipitate and supernatant solutions dialyzed against distilled water. The 'soluble' peptide recovered after lyophilization was 42.4 mg; the 'insoluble' peptide was 59.5 mg. The S-sulfonated B-chain peptides were further purified by preparative HPLC using a C-18 reverse-phase column and 0.1% TFA-water-acetonitrile solvent system.

(iii) Chain Combination

The synthetic H2 hRLX A (1-24) and H2 hRLX B (−1-24) peptides were combined using the procedure described by Chance and Hoffmann (Australian Patent Application No. 68844/81) for insulin chains wherein the S-sulfonated peptides were mixed in a ratio of A:B of 2.6:1 at a peptide concentration of 10 mg/ml in glycine buffer pH 10.5. Dithiothreitol in glycine buffer was then added in an amount to give a total of 1.0 sulfhydryl groups for each S-sulfo group. The reaction mixture was then stirred in an open vessel for 24 hours.

As a further modification to this procedure we have found that the chain combination reaction to form biologically active relaxin proceeded efficiently when one or preferably both of the peptide chains are used as their S-thioethyl-Cys derivatives rather than in the S-sulfo form specified by Chance and Hoffmann (op.cit.) in the case of insulin. The use of S-thioethyl Cys peptides eliminates a reaction and purification step required to convert the peptides to the S-sulfo derivatives. In our experience the S-sulfonation reaction of relaxin peptides is accompanied by side reactions which render the S-sulfo peptides difficult to purify resulting in low yields.

Using the above conditions chain combination yields from 1.5 to 6.0% have been achieved as measured by biological activity in the rat uterine contractility assay of Wiqvist & Paul (Acta Endocrinol., 29, 135–136, 1958).

Example of Chain Combination Reaction

Human relaxin H2 [S-thioethyl $Cys^{10,11,15}$] A(1-24) (4.2 mg dry wt., 2.4 mg peptide by amino acid analysis, 0.84 μmole) was dissolved in 500 μl of 0.1M glycine buffer pH 10.5 in a 3 ml stoppered plastic centrifuge tube. Human relaxin H2 [S-sulfo $Cys^{10,11}$] B(−1-24) (1.60 mg, 1.60 mg peptide by amino acid analysis, 0.33 μmole) dissolved in 200 μl of 0.1M glycine buffer pH 10.5 was added and the mixture agitated. An aliquot (23.0 μl, 2.21 μmole DTT) of a stock solution of dithithreitol (DTT) made up in 0.1M glycine buffer pH 10.5 (0.96 μmole DTT in 10 μl) was added to the peptide solution and following a brief agitation the reaction mixture was allowed to stand at 4° C. for 24 hours open to the air. The mixture was then centrifuged and aliquots of the supernatant solution tested for relaxin biological activity in the rat uterine contractility assay. Aliquots of the reaction mixture inhibited the spontaneous contractions of the rat uterus in a dose-related manner. A 75 μl aliquot completely inhibited uterine contractions equivalent to a chain combination yield of 5.3% as compared to a native pig relaxin A22 B31 standard.

Synthesis of Authentic Human Relaxin H2: hRLX A(1-24)-B(−1-32)

(i) Synthesis of Full Length H2 Human Relaxin B-chain: hRLX B(−1-32)

The amino acid sequence corresponding to residues −1 to +32 of the full length H2 human relaxin B-chain was synthesised using the procedures described above and commencing with 6.4 gm N-α-tertiarybutyloxycarbonyl-L-leucine phenyl acetamido methyl polystyrene resin with a loading of 0.23 mmol Leu per gm. The side-chain protecting groups used for the A(1-24) and B(−1-24) peptides were also employed for the full length B-chain including the S-ethyl mercapto derivative for both cysteines at positions 10 and 22. A modification of this strategy was the use of the N-formyl derivative of BOC-L-tryptophan for coupling at sequence positions 27 and 2.

The final weight of the peptide-resin following chain assembly was 8.2 gm. A portion of the peptide resin (4.0 gm) was treated with anhydrous hydrogen fluoride-anisole as described in previous examples to yield 1.50 gm of crude [S-thioethyl $Cys^{10,22}$, N-formyl $Trp^{2,27}$] hRLX B(−1-32). The crude peptide was purified by gel filtration on BioGel P6 in 0.1M acetic acid. The major peaks eluting from the gel filtration column were characterised by amino acid analysis. The fractions with analyses consistent with the −1 to +32 peptide sequence were collected and lyophilised. Deformylation of the tryptophan residues was effected by treating the peptide (100 mg) with sodium hydroxide solution (5 ml) pH 11.5 for 5 min. during which time the peptide precipitated from solution. The reaction mixture was neutralised to dissolve the peptide and applied directly to a BioGel P6 column in 0.1M acetic acid. Removal of the formyl groups from tryptophan was monitored by UV spectroscopy by following the disappearance of the N-formyl absorption at 300 nm and the appearance of the characteristic tryptophan spectra with an absorption maximum at 280 nm. Peptide fractions eluting from the column with the correct amino acid anlysis were collected and lyophilised.

Attempts to further purity the [S-thioethyl $Cys^{10,22}$] hRLX B(−1−32) peptide by preparative HPLC were not successful because of loss of peptide by adsorption to the column media. Peptide purified by gel chromatography was used directly in chain combination experiments.

(ii) Chain Combination of A(1-24) with B(−1-32): Preparation of Human Relaxin H2

The synthetic S-sulfonated and S-thioethyl H2 human relaxin A(1-24) peptides were coupled to S-thioethyl H2 human relaxin B(−1-32) using the same chain combination procedures described previously for the shortened B-chain (−1-24). Samples of the recombination mixture were tested for relaxin biological activity in the rat uterine contractility assay. Aliquots of the reaction mixture inhibited the spontaneous contractions of the rat uterus in a dose-related manner. A 100 μl aliquot completely inhibited uterine contractions equivalent to a chain combination yield of 3.0% as compared to a native pig relaxin A22 B31 standard.

References

Anderson, M. L., Long, J. A. and Hayashida, T. Immunofluorescence studues on the localisation of relaxin in the corpus luteum of the pregnant rat. Biol. Reprod. 13, 499–504 (1975).

Barany, G. and Merrifield, R. B., In "The Peptides", Ed. E. Gross & J. Meienjofer, Academic Press, New York, pp. 1–283 (1980).

Beaucage, S. L. and Caruthers, M. H. Tetrahedron Lett. 22, 1859–1862 (1981).

Chang, A. C. Y. Nature 275, 617–624 (1978).

Chirgwin, J. M., Przybyla, A. E., MacDonald, R. J. and Rutter, W. J., Isolation of biologically active ribonucleic acid from sources enriched in ribonuclease. Biochem. 18, 5294–5299, (1979).

Du et al, Scientia, Sinica, 10I, 84–104 (1961).

Haley, J., Hudson, P., Scanlon, D., John, M., Cronk, M., Shine, J., Tregear, G. and Niall, H. DNA 1, 155–162 (1982).

Hisaw, F. L. Proc. Soc. Exp. Biol. Med. 23, 661–663 (1926).

Hudson, P., Haley, J., Cronk, M., Shine, J. and Niall, H. Nature, 291, 127–131 (1981).

Hudson, P., Haley, J., John, M. Cronk, M., Crawford, R., Haralambidis, J., Tregear, G., Shine, J. and Niall, H. Structure of a genomic clone encoding biologically active human relaxin. Nature 301, 628–631 (1983). Huynh, T., Saint, R. and Davis R. (1983) personal communication.

James, R., Niall, H., Kwok, S. and Bryant-Greenwood, G. Nature, 267, 544–546 (1977).

John, M. J., Walsh, J. R., Borjesson, B. W. and Niall, H. D. Endocrinology 108, 726–729 (1981).

Lawn, R. M., Fritsch, E. F., Parker, R. C., Blake, G. and Maniatis, T. all 15, 1157–1174 (1978).

Maxam, A. M. and Gilbert, W. (1977) A new method for sequencing DNA. Proc. Natl. Acad. Sci. USA 74, 560–564.

Morrison, D. A., In: Methods in Enzymology, R. Wu, ed. (New York: Academic Press) pp. 326–331 (1979).

Roychoudhury, R. Jay, E. and Wu, R. (1976) Terminal labelling and addition of homopolymer tracts to duplex DNA fragments by terminal deoxynuclecotidyl transferase. Nucleic Acid Res. 3, 863–877 (1976).

Sanger, F., Coulson, A. R., Barrell, B. G., Smith, A. J. H. and Roe, B. A., J. Mol. Biol. 143, 161–178 (1980).

Schwabe, C., Gowan, L. K. and Reinig, J. W., Ann. N.Y. Acad. Sci. 380, 6–12 (1982).

Schwabe, C., McDonald, J. K. and Steinetz, B. C. Biochem. Biophys. Res. Commun. 75, 503–510 (1977).

Southern, E. M., J. Mol. Biol. 98, 503–517 (1975).

Taylor, J. M., Illmersee, R., and Summers, J.Biochim. Biophys. Acta 442, 324–330 (1976).

Ullrich, A., Shine, J., Chirgwin, J., Picket, R., Tischer, E., Rutter, W. J. and Goodman, H. M. Rat insulin genes: construction of plasmids containing the coding sequences. Science 196, 1313–1319 (1977).

Vogt, V. M. Purification and further properties of single-strand-specific nuclease from *Aspergillus oryzae*. Eur. J. Biochem. 33, 192–200 (1973).

Wickers, M. P., Buell, G. N. and Schimke, R. T. Synthesis of double-stranded Dna complementary to lysozyme, ovomucoid, and ovalbumin mRNAs. J. Biol. Chem. 253, 2483–2495 (1978).

Wiqvest & Paul, Acta Endocrinol., 29:135–136 (1958).

We claim:

1. A process for synthesizing human H2-prorelaxin comprising A and B peptides separated from each other by a C peptide, comprising incubating a microorganism, transformed by an expression transfer vector comprising a deoxynucleotide sequence coding for said human H2-prorelaxin under conditions suitable for expression of said sequence coding for said human H2-prorelaxin, and purifying said human H2-prorelaxin from a lysate or culture medium of said microorganism.

2. A process for synthesizing human H2-relaxin comprising A and B peptides, comprising incubating a microorganism, transformed by an expression transfer vector comprising the deoxynucleotide sequence coding for human H2 -relaxin under conditions suitable for expression of said sequence coding for said human H2-relaxin, and purifying human H2-relaxin from a lysate or culture medium of said microorganism.

3. A process for making a fusion protein having, as its C-terminal sequence, a polypeptide comprising:

(i) a H2-relaxin A chain selected from the group consisting of A(1-24) to A(5-24), wherein amino acids 1-24 have the following sequence:

```
     1              5                  10
    Gln Leu Tyr Ser Ala Leu Ala Asn Lys Cys Cys His 15                  20            24
    Val Gly Cys Thr Lys Arg Ser Leu Ala Arg Phe Cys;
```

(ii) a H2-relaxin B chain selected from the group consisting of B(−1−32) to B(4−23), wherein amino acids −1−32 have the following sequence:

```
   −1  1                 5                    10
  Asp Ser Trp Met Glu Glu Val Ile Lys Leu Cys Gly Arg 15                  20
  Glu Leu Val Arg Ala Gln Ile Ala Ile Cys Gly Met 25        30   32
       Ser Thr Trp Ser Lys Arg Ser Leu; and
```

(iii) a human H2-prorelaxin C chain having the amino acid sequence as set forth in FIGS. 2A through 2D as arranged in FIG. 2, wherein the C chain amino acid sequence is modified at the junction of the B/C and C/A chains to facilitate cleavage at the B/C and C/A junctions and subsequent excision of the C chain, and as its N-terminal sequence, a portion of a prokaryotic protein, comprising incubating a microorganism transformed by an expression transfer vector comprising an appropriate deoxynucleotide sequence encoding said fusion protein.

4. The process according to claim 3, wherein the C-terminal sequence of said fusion protein consists essentially of a H2-relaxin A chain selected from the group consisting of A(1−24) to A(3−24) and a H2-relaxin B chain selected from the group consisting of B(−1−32) to B(−1−24).

5. A fusion protein having, as its C-terminal sequence, a polypeptide comprising:

(i) a H2-relaxin A chain selected from the group consisting of A(1−24) to A(5−24), wherein amino acids 1−24 have the following sequence:

```
       1              5                    10
   Gln Leu Tyr Ser Ala Leu Ala Asn Lys Cys Cys His 15              20           24
       Val Gly Cys Thr Lys Arg Ser Leu Ala Arg Phe Cys;
```

(ii) a H2-relaxin B chain selected from the group consisting of B(−1−32) to B(4−23), wherein amino acids −1−32 have the following sequence:

```
   −1  1                 5                    10
  Asp Ser Trp Met Glu Glu Val Ile Lys Leu Cys Gly Arg 15                  20
  Glu Leu Val Arg Ala Gln Ile Ala Ile Cys Gly Met 25        30   32
       Ser Thr Trp Ser Lys Arg Ser Leu;
```

(iii) a human H2-prorelaxin C chain having the amino acid sequence as set forth in FIGS. 2A through 2D as arranged in FIG. 2, wherein the C chain amino acid sequence is modified at the junction of the B/C and C/A chains to facilitate cleavage at the B/C and C/A junctions and subsequent excision of the C chain, and as its N-terminal sequence, a portion of a prokaryotic protein.

6. The fusion protein according to claim 5, wherein the C-terminal sequence of said fusion protein consists essentially of a H2-relaxin A chain selected from the group consisting of A(1−24) to A(3−24) and a H2-relaxin B chain selected from the group consisting of B(−1−32) to B(−1−24).

* * * * *